United States Patent [19]
Anderson et al.

[11] Patent Number: 6,123,720
[45] Date of Patent: Sep. 26, 2000

[54] STENT DELIVERY SYSTEM WITH STORAGE SLEEVE

[75] Inventors: Curtis E. Anderson, Crystal; Brian J. Brown, Hanover, both of Minn.

[73] Assignee: SciMed Life Systems, Inc., Maple Grove, Minn.

[21] Appl. No.: 09/118,644

[22] Filed: Jul. 17, 1998

Related U.S. Application Data

[62] Division of application No. 08/699,533, Aug. 19, 1996, Pat. No. 5,800,517.

[51] Int. Cl.$^7$ ...................................................... A61F 2/06
[52] U.S. Cl. ................................ 623/1; 606/194; 606/195
[58] Field of Search .................................. 623/1, 11, 12; 606/192, 194, 195, 198, 108, 200, 191; 604/198

[56] References Cited

U.S. PATENT DOCUMENTS

| | | |
|---|---|---|
| 3,911,927 | 10/1975 | Rich et al. . |
| 3,996,938 | 12/1976 | Clark, III ................................ 606/198 |
| 4,328,811 | 5/1982 | Fogarty . |
| 4,572,186 | 2/1986 | Gould et al. . |
| 4,606,347 | 8/1986 | Fogarty et al. . |
| 4,650,466 | 3/1987 | Luther ..................................... 606/198 |
| 4,655,771 | 4/1987 | Wallsten . |
| 4,665,918 | 5/1987 | Garza et al. . |
| 4,681,110 | 7/1987 | Wiktor . |
| 4,699,611 | 10/1987 | Bowden . |
| 4,732,152 | 3/1988 | Wallsten et al. . |
| 4,733,665 | 3/1988 | Palmaz . |
| 4,848,343 | 7/1989 | Wallsten et al. . |
| 4,863,440 | 9/1989 | Chin . |
| 4,875,480 | 10/1989 | Imbert . |
| 4,922,905 | 5/1990 | Strecker . |
| 4,954,126 | 9/1990 | Wallsten . |
| 4,990,138 | 2/1991 | Bacich et al. . |
| 5,015,231 | 5/1991 | Keith et al. . |
| 5,026,377 | 6/1991 | Burton et al. . |
| 5,061,275 | 10/1991 | Wallsten et al. . |
| 5,064,435 | 11/1991 | Porter . |
| 5,071,407 | 12/1991 | Termin et al. . |
| 5,074,845 | 12/1991 | Miraki et al. . |
| 5,078,720 | 1/1992 | Burton et al. . |
| 5,137,512 | 8/1992 | Burns et al. . |
| 5,158,548 | 10/1992 | Lau et al. . |
| 5,192,297 | 3/1993 | Hull . |
| 5,201,757 | 4/1993 | Heyn et al. . |
| 5,234,457 | 8/1993 | Andersen . |
| 5,242,399 | 9/1993 | Lau et al. . |
| 5,261,878 | 11/1993 | Galindo . |
| 5,306,294 | 4/1994 | Winston et al. ......................... 606/195 |
| 5,342,307 | 8/1994 | Euteneuer et al. . |
| 5,352,236 | 10/1994 | Jung et al. . |
| 5,360,401 | 11/1994 | Turnland . |
| 5,445,646 | 8/1995 | Euteneuer et al. . |
| 5,534,007 | 7/1996 | St. Germain et al. ................. 605/198 |
| 5,571,135 | 11/1996 | Fraser et al. . |
| 5,765,682 | 6/1998 | Bley et al. .............................. 206/363 |
| 5,766,203 | 6/1998 | Imran et al. ............................. 606/194 |
| 5,776,141 | 7/1998 | Klein et al. ............................. 606/195 |
| 5,788,707 | 8/1998 | Del Toro et al. ....................... 606/198 |
| 5,800,517 | 9/1998 | Anderson et al. .......................... 623/1 |
| 5,807,398 | 9/1998 | Shaknovich ............................. 606/194 |
| 5,810,838 | 9/1998 | Solar ....................................... 606/198 |
| 5,810,871 | 9/1998 | Tuckey et al. .......................... 606/198 |
| 5,824,041 | 10/1998 | Lenker et al. ........................... 606/195 |

FOREIGN PATENT DOCUMENTS

| | | |
|---|---|---|
| 0 696 447 A2 | 2/1996 | European Pat. Off. . |
| WO95/31945 | 11/1995 | WIPO . |

*Primary Examiner*—Mickey Yu
*Assistant Examiner*—Tram A. Nguyen
*Attorney, Agent, or Firm*—Vidas, Arrett & Steinkraus, P.A.

[57] ABSTRACT

A delivery system for implantation of a medical device in a body lumen including an elongate flexible catheter for delivering the medical device to a predetermined location in a lumen. The medical device surrounds the flexible catheter near its distal end and is held in a delivery configuration where the medical device has a reduced radius along its axial length by a storage sleeve. The storage sleeve surrounds the medical device. Where the catheter has an outer sleeve, the storage sleeve not only provides a means for retaining the medical device in its delivery configuration, but also protects the outer sleeve from creep during storage and/or elevated temperature conditions. The storage sleeve is removed from the system prior to use.

20 Claims, 3 Drawing Sheets

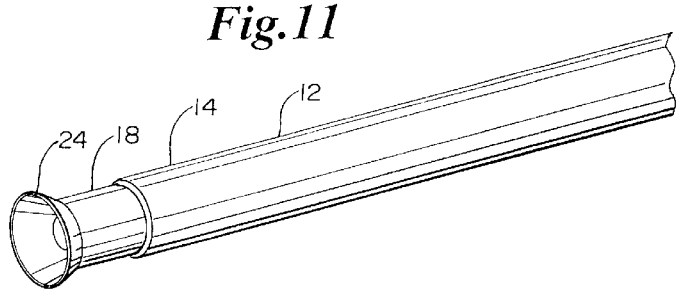
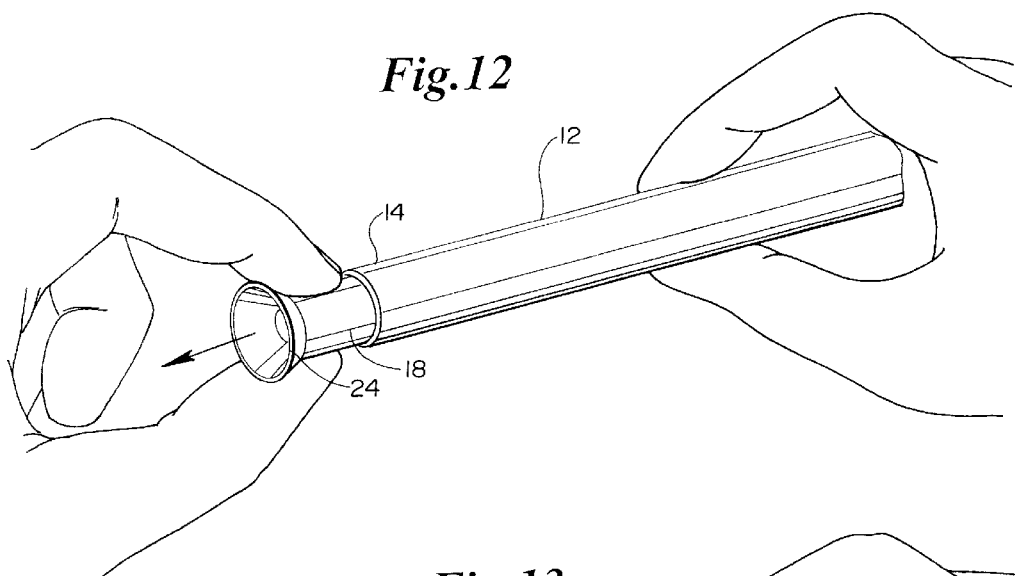
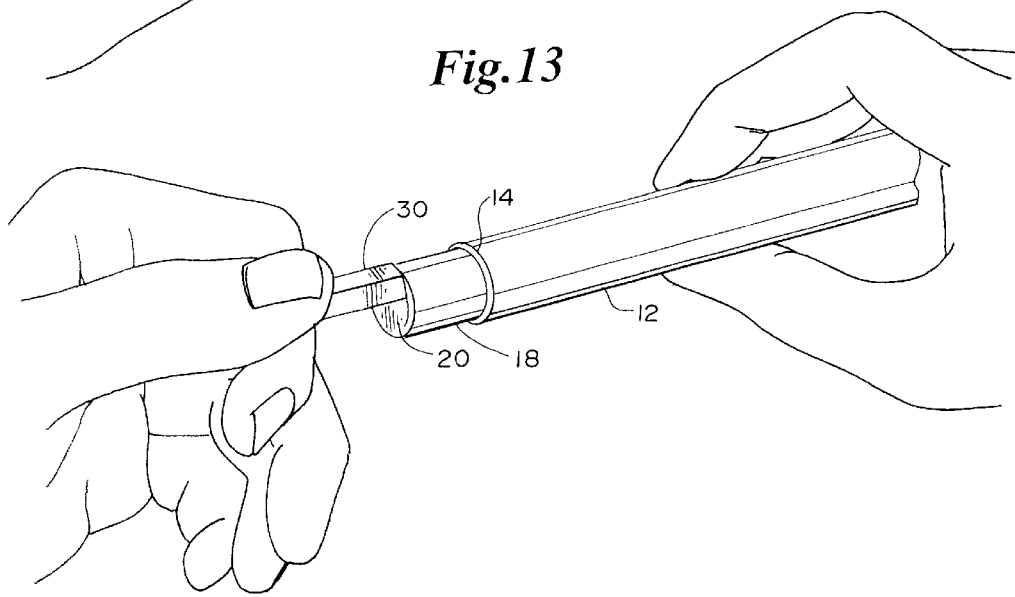

STENT DELIVERY SYSTEM WITH STORAGE SLEEVE

This application is a Divisional of U.S. application Ser. No. 08/699,533, filed Aug. 19, 1996, now U.S. Pat. No. 5,800,517, incorporated herein by reference.

BACKGROUND OF THE INVENTION

1. Field of the Invention

The present invention relates to delivery systems for delivering and deploying medical devices such as stents. More specifically, the invention relates to a medical device delivery system having an outer sleeve, and a storage sleeve located between the outer sleeve and the medical device. The medical device may include all self-expanding catheter delivered prosthetics, including stents and IVC filters, or the like, including medical devices of utility in any body lumen, including the esophagus, urethra, ureter, biliary tract, blood vessels or other body lumens.

2. Description of the Related Art

Stents and delivery systems for deploying stents are a highly developed and well known field of medical technology. Stents have many well known uses and applications. A stent is a prosthesis which is generally tubular and which is expanded radially in a vessel or lumen to maintain its patency. Stents are widely used in body vessels, body canals, ducts or other body lumens.

The preferred present stent delivery apparatus may be utilized with any self-expanding stents, which are known in the art. A well known self-expanding stent is the woven braided stent disclosed in U.S. Pat. Nos. 4,655,771 (Wallsten); 4,954,126 (Wallsten) and 5,061,275 (Wallsten), although any type of self-expanding stent may be deployed using the inventive delivery system and method. A preferred stent for use with the stent delivery system of the present invention is described in co-pending PCT Application PCT/US95/06228 directed to "Improved Tissue Supporting Devices", incorporated herein by reference.

The delivery systems for stents are generally comprised of catheters with the stent axially surrounding the distal end of the catheter. It is highly desirable to keep the profile of the catheter as small as possible. Therefore, self-expanding stents are generally confined in a reduced radius for delivery to the deployment site. Once the stent is deployed the catheter is removed, leaving the stent implanted at the desired location to keep the vessel walls from closing.

A variety of techniques have been developed for holding a self-expanding stent in its reduced configuration while moving the distal end of the catheter to the deployment site. For example, in U.S. Pat. No. 4,655,771 (Wallsten), gripping members at either end of the stent hold the stent in an axially-elongated position, which causes the stent to take a reduced radius delivery configuration.

Another common technique for maintaining the self-expanding stent in a reduced radius delivery configuration is using a sheath which surrounds the stent and compresses it around the catheter. This technique is disclosed in U.S. Pat. No. 5,071,407 (Termin) and U.S. Pat. No. 5,064,435 (Porter), both of which use a silicon rubber sheath to compress the stent. A similar technique is disclosed in U.S. Pat. No. 5,026,377 (Burton) and U.S. Pat. No. 5,078,720 (Burton).

A variation on surrounding the stent with a sheath is disclosed in U.S. Pat. No. 4,732,152 (Wallsten); U.S. Pat. No. 4,848,343 (Wallsten) and U.S. Pat. No. 4,875,480 (Imbert), all of which disclose using a sleeve formed of a doubled-over section of membrane to compress and contain the stent.

U.S. Pat. No. 5,234,457 discloses using a sheath to surround a mesh stent of the type disclosed in U.S. Pat. No. 4,922,405. However, in this patent the sheath is not used to compress the stent, but is used to prevent fluid from accessing the stent. The stent is impregnated with a pure gelatin or other dissolvable material which, when cured, has sufficient strength to hold the stent in its reduced delivery configuration. Once the sheath is withdrawn, the stent is exposed to the body fluids which dissolve the gelatin, allowing the stent to self-expand. This reference also discloses using axial distribution of gelatins with different rates of thermal decomposition to control the physical profile of the stent as it expands. However, using an impregnated mesh stent adds several inconvenient manufacturing steps to the process of preparing the stent for implantation.

In addition, none of the prior art methods of containing self-expanding stents address the problems associated with storage. For example, the outer sleeve of prior delivery systems can creep during storage and/or under elevated temperature conditions due to the expansion forces of the stent onto the inner diameter of the sleeve. As storage temperatures increase, for example, certain stenting materials such as nitinol, become stronger. Such a self expanding stent could conceivably expand during storage and not only deform the outer sleeve, but also become unsuitable for use due to its expansion.

There remains a need in the art for a stent delivery system in which the outer sleeve and the stent are retained in place for the purposes of storage, thereby preserving the shape of the stent and the sleeve. Furthermore, there remains the need for a stent delivery system in which the profile of the delivery catheter is retained in storage.

SUMMARY OF THE INVENTION

Accordingly, the present invention provides a stent delivery apparatus including means for removing the storage load of a stent from the outer sheath. The inventive stent delivery device includes a catheter with a self-expanding stent held in a reduced delivery configuration for insertion and transport through a body lumen to a predetermined site for deployment. The stent is held by a storage sleeve which is removable prior to use of the stent delivery apparatus.

The present invention therefore contemplates any stent delivery device in combination with a storage sleeve. The inventive storage sleeve may be used with any device having an outer sleeve that retracts from a stent, including a stent delivery apparatus with a slipping sleeve, i.e. rolling membrane, sliding sleeve, a doubled over section of membrane, or a section of membrane folded onto itself. The preferred embodiment is a stent delivery system with a pull back outer sleeve design which has a tubular storage sleeve placed between the outer sleeve and the stent. The stent is held in the delivery configuration by the tubular storage sleeve, which also protects the outer sleeve from creep during storage and elevated temperature conditions.

The tubular storage sleeve of the present invention will prevent a stent from becoming embedded in a pull-back sleeve. This allows for the use of a "weak" pull back sleeve. The storage sleeve can be used under or over a pull back sleeve.

In storage, the storage sleeve will hold the stent in its delivery configuration in an environment having a temperature of up to about 150–160° F.

An alternate embodiment of the stent delivery device includes a storage sleeve with a distal end closure, i.e. a storage cap, to provide a watertight seal for the stent. A further alternative embodiment includes a flare at the distal end.

The storage sleeve or cap may be made of a metallic material or a polymeric material. One or more surfaces of the sleeve or cap may include a teflon, hydrophobic or hydrophilic coating to simplify its removal prior to use of the stent delivery system. A storage sleeve or cap according to the present invention may include a magnet in association with the distal end closure to simplify removal of the cap.

The invention may also be used with a device for delivery of non self-expanding stents by placing the storage sleeve or cap between the outer sleeve and the stent, which is placed around an expandable balloon. Alternatively, the storage sleeve or cap may be placed over a stent delivery apparatus without an outer sleeve. Further, the invention may be used with a single layer hydraulic sheath stent delivery apparatus such as is disclosed in U.S. patent application Ser. No. 08/245,919 filed May 19, 1994, a continuation-in-part of application Ser. No. 08/141,269 filed Oct. 22, 1993, the disclosures of which are hereby incorporated herein by reference.

The invention may also be used with medical devices including but not limited to all self-expanding catheter delivered prosthetics, including stents and IVC filters, or the like, including medical devices of utility in any body lumen, including the esophagus, urethra, ureter, biliary tract, blood vessels or other body lumens.

BRIEF DESCRIPTION OF THE DRAWINGS

A detailed description of the invention is hereafter described with specific reference being made to the drawings in which:

FIG. 11 is a perspective view of the distal portion of a stent deployment device according to the present invention; and FIGS. 12 and 13 are perspective views as in FIG. 11 showing alternative methods of removal of the storage sleeve.

DESCRIPTION OF THE PREFERRED EMBODIMENTS

Figure 2:
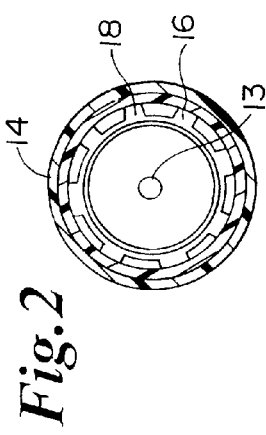
FIG. 2 is a schematic cross-section of the apparatus shown in FIG. 1, taken along line 2—2.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The present invention provides in one form a stent delivery apparatus including a catheter, a self-expanding stent held in reduced delivery configuration for insertion and transport through a body lumen to a predetermined site for deployment. The inventive stent delivery apparatus further includes means for removing the storage load of a stent from the outer sheath, a storage sleeve which is removable prior to use of the stent delivery apparatus.

The present invention therefore contemplates any stent delivery device in combination with a storage sleeve. The inventive storage sleeve may be used with any device having an outer sleeve that constrains a stent to its delivery configuration during storage and during delivery to its deployment site within the body, and is removed from the stent for stent deployment, including a stent delivery apparatus with a slipping sleeve i.e. rolling membrane, sliding sleeve or doubled over section of membrane. The preferred embodiment is a stent delivery system with a pull back outer sleeve design which has a tubular storage sleeve placed between the outer sleeve and the stent. The stent is held substantially in its delivery configuration by the tubular storage sleeve, which also protects the outer sleeve from creep during storage and elevated temperature conditions of up to about 150–160° F.

The present invention also contemplates the use of a storage sleeve as described with any delivery apparatus for balloon expandable NiTi stents, including those without an outer sleeve. The invention may also be used with medical devices including but not limited to all self-expanding catheter delivered prosthetics, including stents and IVC filters, or the like, including medical devices of utility in any body lumen, including the esophagus, urethra, ureter, biliary tract, blood vessels or other body lumens.

Figure 1:
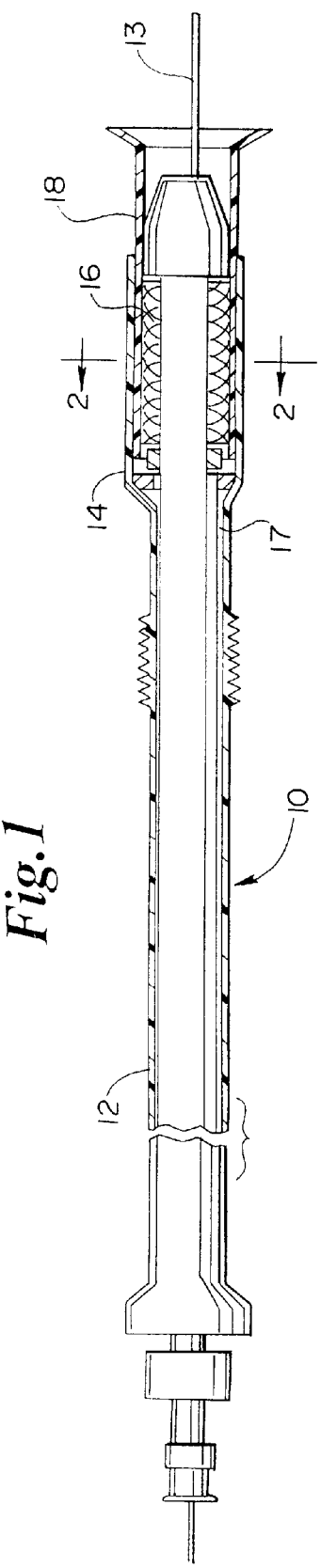
FIG. 1 is a schematic depiction of a medical device delivery apparatus according to the present invention, with radially expandable medical device and storage sleeve carried within a catheter sheath.

Referring now to the figures, FIG. 1 provides a schematic depiction of a stent delivery apparatus, shown generally at 10, which is used to deliver a stent in a reduced radius delivery configuration to a deployment site in a body according to the present invention. The distal portion of apparatus 10 is shown in cross section in FIG. 2. Apparatus 10 includes an elongate flexible catheter 12, with a guide wire 13. In the preferred embodiment catheter 12 is extruded of biocompatible materials such as polyimide, surlyn, teflon or polyethylene. Other suitable materials for catheter 12 include nylons, urethanes, and polypropylene materials which are preferably compatible with silicone and/or hydrophilic coatings. It should be understood that while a hydrophilic coating is preferred, any biocompatible material may be used. The catheter materials, while not themselves hydrophilic can be coated with a hydrophilic material. Therefore, it can be seen that any biocompatible material can be used to make catheter 12. As will be discussed below, the inventive stent delivery apparatus allows for the outside diameter of the catheter to be 5.3 French (F) (0.060 inches or 1.52 mm) or less using a 0.014 inch guide wire.

The distal end portion of catheter 12 has a pull back outer sleeve 14 which encases stent 16 and is actuated/retracted by pull wire 17. Stent 16 is a self-expanding stent, and in the preferred embodiment is a shape memory alloy (Nitinol)

slotted tube stent. However, the disclosed stent delivery apparatus will deliver any type of self-expanding stent, such as for example, a so called woven braided stent of a type somewhat similar to those disclosed in Wallsten U.S. Pat. No. 4,655,771; Wallsten U.S. Pat. No. 4,954,126 and Wallsten U.S. Pat. No. 5,061,275. Stent 16 is shown confined in its reduced radius delivery configuration by the inventive storage sleeve 18, located between stent 16 and outer sleeve 14. Storage sleeve 18 surrounds the outer diameter of stent 16 and is covered by the inner diameter of outer sleeve 14. FIG. 2 is a schematic cross-section of the apparatus shown in FIG. 1, taken along line 2—2.

Storage sleeve 18 may be made of any metal, polymeric or composite material. Although storage sleeve 18 does not contact the body it must be biocompatible as there is a possibility that storage sleeve 18 could contact stent 16 during removal and leave traces of the material of which the sleeve is made on the stent.

Storage sleeve 18 could be made of any biocompatible alloy, such as stainless steel, titanium, tantalum, nitinol, elgiloy, and the like, stainless steel being most preferred. Storage sleeve 18 could be made by any suitable process for forming metal, the most preferred being stamping or rolling.

Storage sleeve 18 may also be made of a biocompatible polymeric material, such as polyimides, teflons, polyolefins, nylons, and the like, polyimides being most preferred. Storage sleeve 18 of polymeric material could be made by any suitable process, the most preferred being extrusion if the material is a thermoplastic or by other suitable process if the material is a thermoset polymer. Storage sleeve 18 may also be made of molded plastic, such as polyolefin copolymer (POC) SURLYN™, fluoropolymers, non-compliant polyethylene terephthalate (PET); polyimide, nylon, polyethylene or the like.

Alternatively, such a sleeve may be commercially available. For example, storage sleeve 18 may be made of a piece of metallic or polymeric tubing cut to a predetermined length.

Figure 3:
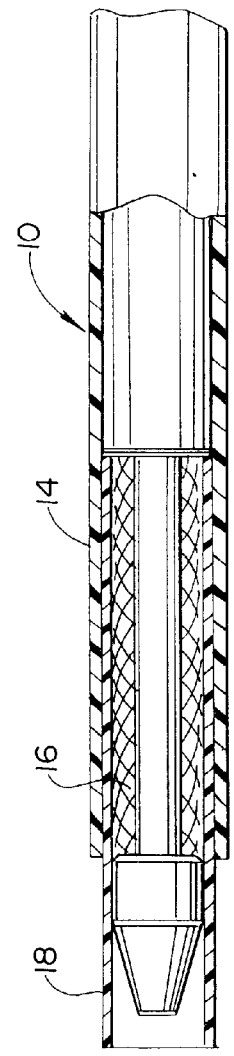
FIG. 3 is a fragmentary view of a stent deployment device according to the present invention with storage sleeve between the outer sleeve and the stent.
Figure 4:
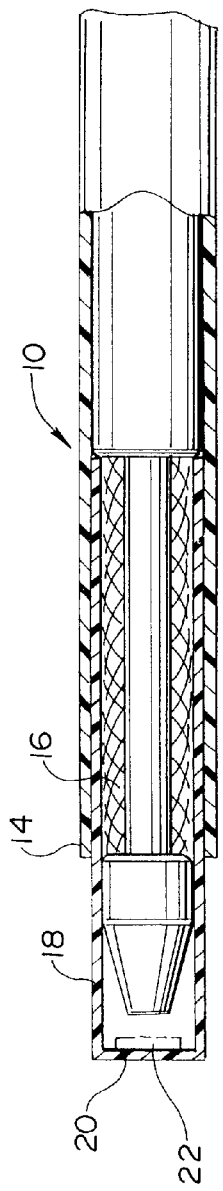
FIGS. 4–6 are fragmentary views as in FIG. 3 showing alternative embodiments of the storage sleeve between the outer sleeve and the stent.
Figure 5:
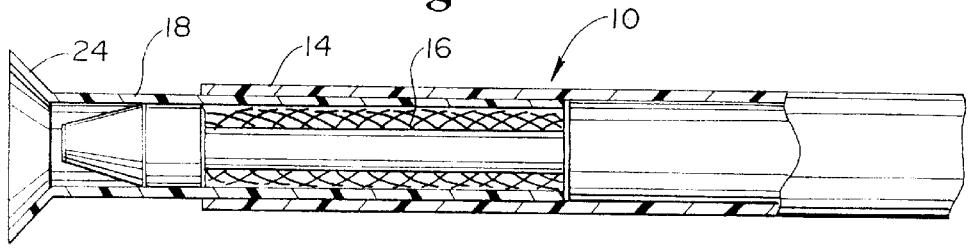
Figure 6:
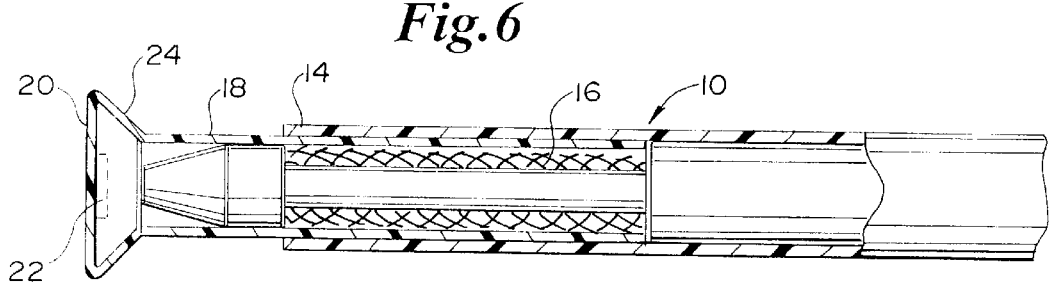

Referring now to FIGS. 3–6, outer sleeve 14 is shown in a partially uncovered position for better view of storage sleeve 18. FIG. 3 is a fragmentary view of the device as in FIG. 1 showing storage sleeve 18. FIGS. 4–6 show alternative embodiments of storage sleeve 18. In FIG. 4, storage sleeve 18 has an optional distal end closure 20. Storage sleeve 18 and end closure 20 may be unitary in construction, i.e., a cap, and may be produced by the methods noted above. Storage sleeve 18 with optional end closure 20 provides a watertight seal for stent 16 during storage.

A storage sleeve according to the present invention may optionally include a magnet in association with its distal end to simplify its removal. The storage sleeve would be removable by using a magnet external of the stent delivery device. Storage sleeve 18, is shown at FIGS. 4 and 6 having a magnet 22 located at its distal end portion. Storage sleeve 18 as shown at FIG. 4 may include a magnet 22 located at end closure 20. Where storage sleeve 18 is made of a metal alloy or polymer, end closure 20 may alternatively be a magnet.

An alternative embodiment of storage sleeve 18, shown at FIG. 5, includes grasping means 24 to prevent placement in the body with the sleeve. Grasping means 24 can be of any suitable shape. At FIG. 5, grasping means 24 is a flare. The storage sleeve shown at FIG. 6 includes end closure 20 and grasping means 24. At FIG. 8, grasping means 24 is a ring. Alternatively, one or more surfaces of storage sleeve 18 may include a Teflon® or other lubricious coating to simplify its removal prior to use of the stent delivery apparatus.

Figure 10:
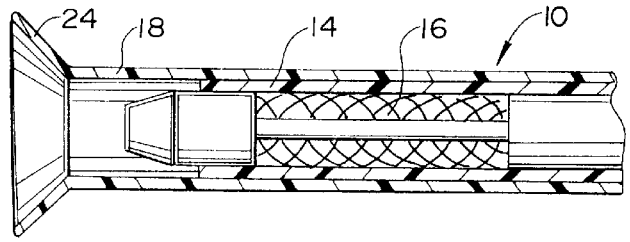
FIG. 10 is a fragmentary view of a stent deployment device according to the present invention with storage sleeve covering the outer diameter of the stent and delivery catheter, wherein the storage sleeve is being removed.

Alternatively, the storage sleeve or cap may be placed over a stent delivery apparatus with an outer sleeve. FIG. 10 shows a stent deployment device according to the present invention wherein storage sleeve 18 covers the outer diameter of outer sleeve 18 and stent 16.

Figure 7:
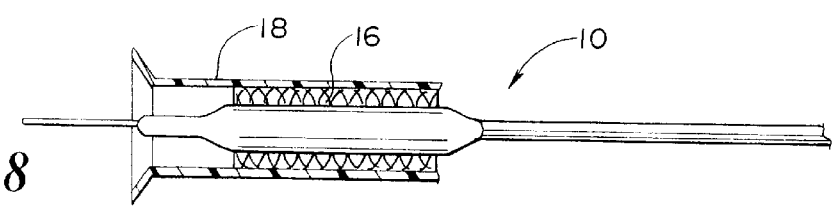
FIG. 7 is a fragmentary view of a medical device delivery apparatus according to the present invention, with radially expandable medical device and storage sleeved carried thereon.

Further, storage sleeve 18 may be used with a stent delivery apparatus having no outer sleeve, as shown in FIG. 7. Storage sleeve 18 would protect a stent by preventing dislodgement and would prevent expansion of a stent such as a NiTi stent, not only during storage prior to delivery, but also during sterilization.

Figure 8:
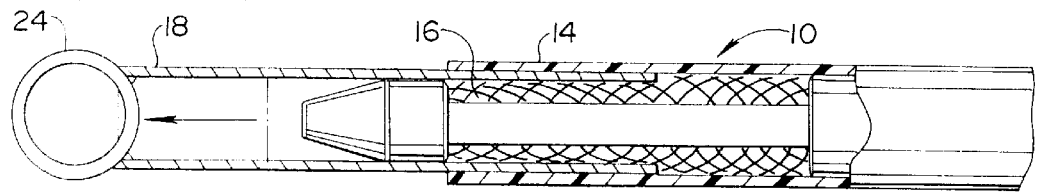
FIGS. 8–9 are fragmentary views as in FIGS. 3–6 showing alternative embodiments of the storage sleeve between the outer sleeve and the stent, wherein the storage sleeves are being removed.
Figure 9:
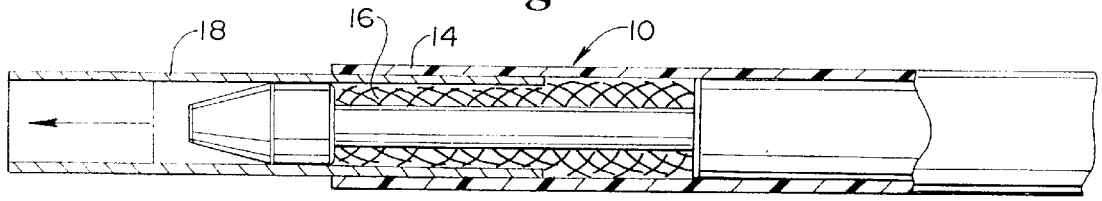

At FIGS. 8–10, a storage sleeve 18 is shown being removed. Removal is shown in further detail at FIGS. 11–13. FIG. 11 is a fragmentary perspective view of catheter 12, showing pull back outer sleeve 14 and storage sleeve 18. As shown in FIG. 12, storage sleeve 18 may be removed by grasping its end and removing it from catheter 12. As shown in FIG. 13, where storage sleeve 18 includes a magnet in association with its distal end, storage sleeve 18 may be removed by using an external magnet 30.

The invention may also be used with a device for delivery of non self-expanding stents by placing the storage sleeve or cap between the outer sleeve and the stent, which is placed around an expandable balloon such as balloon expandable shape memory alloy (nitinol) stent as disclosed in PCT/US95/06228, where elevated storage temperatures may cause expansion of the stent. The storage sleeve may also be used with any delivery apparatus for balloon expandable NiTi stents, including those without an outer sleeve. Further, the invention may be used with a single layer hydraulic sheath stent delivery apparatus such as is disclosed in U.S. patent application Ser. No. 08/245,919 filed May 19, 1994, a continuation-in-part of application Ser. No. 08/141,269 filed Oct. 22, 1993, the disclosures of which are hereby incorporated herein by reference.

One of the important features of the inventive stent delivery apparatus is that it ensures the retention of the desired delivery configuration of not only the stent, but also the outer sleeve.

The stent delivery system of the present invention provides a means by which the stent is retained in place for the purposes of storage, thereby preserving the shape of the stent and the outer sleeve, and preserving the profile of the delivery catheter and the smooth retraction or removal of the outer sleeve.

The present invention prevents the outer sleeve of the delivery systems from creeping during storage and/or under elevated temperature conditions, and prevents the self-expanding stent from expansion during storage, thereby preventing the self-expanding stent from deforming the outer sleeve and becoming unsuitable for use due to its expansion or the embedding of the stent into its inner surface.

Where the outer sleeve of the delivery system is made of material which will resist deformation by the stent, the storage sleeve may be placed either on the inner diameter or the outer diameter of the outer sleeve of the catheter delivery means. Placing the storage sleeve over the outer sleeve of the catheter delivery means would provide strength to a thin-walled retaining sleeve during storage. A retaining sleeve with a thinner wall provides a lower profile and improved flexibility.

There are many advantages provided by the present invention. The storage sleeve of the present invention will prevent a stent from becoming embedded in a pull-back sleeve. This allows for the use of a "weak" pull back sleeve.

The storage sleeve can be used under or over a pull back sleeve, or even with a balloon expandable medical device having no pull back sleeve.

This completes the description of the preferred and alternate embodiments of the invention. It is to be understood that even though numerous characteristics and advantages of the present invention have been set forth in the foregoing description, together with the details of the structure and function of the invention, the disclosure is illustrative only and changes may be made in detail, especially in matters of shape, size and arrangement of parts within the principles of the invention, to the full extent indicated by the broad, general meaning of the terms in which the appended claims are expressed. Those skilled in the art may recognize other equivalents to the specific embodiment described herein which are intended to be encompassed by the claims attached hereto.

What is claimed is:

1. A delivery system for implantation of a medical device in a vessel, comprising:
    an elongate flexible catheter having proximal and distal ends for delivering a balloon-expandable medical device to a location in a vessel;
    a balloon-expandable medical device having proximal and distal ends, the medical device surrounding and carried by the flexible catheter near the distal end of said catheter, the medical device being in a delivery configuration where the medical device has a reduced radius along an axial length of said medical device;
    a remotely operable retractable sleeve at least partially surrounding the medical device, the retractable sleeve capable of being removed subsequent to implantation of the catheter into a body lumen;
    a retaining and storage sleeve for retaining the medical device in approximately or substantially the delivery configuration, the retaining and storage sleeve comprising a sleeve for retaining the medical device in said delivery configuration, the retaining and storage sleeve surrounding the medical device, and being removable prior to insertion of the distal end of the catheter into a body lumen.

2. The delivery system of claim 1 wherein the retaining and storage sleeve is made of a biocompatible polymeric material.

3. The delivery system of claim 2 wherein the biocompatible polymeric material is selected from the group consisting of polyimides, teflons, polyolefins, and nylons.

4. The delivery system of claim 1 wherein the retaining and storage sleeve is made of a biocompatible metal alloy.

5. The delivery system of claim 4 wherein the biocompatible metal alloy is selected from the group consisting of stainless steel, titanium, tantalum, nitinol, and elgiloy.

6. The delivery system of claim 1 wherein the retaining and storage sleeve further comprises a proximal end, a distal end and an end cap located at the distal end.

7. The delivery system of claim 1 wherein the retaining and storage sleeve further comprises a proximal end and a distal end, the retaining and storage sleeve being enlarged at the distal end thereof.

8. The delivery system of claim 1 further including means for removing the retaining and storage sleeve.

9. The delivery system of claim 1 wherein the retractable sleeve is at least partially disposed about the medical device and the retaining and storage sleeve is further at least partially disposed about the retractable sleeve.

10. The delivery system of claim 1 wherein the retaining and storage sleeve is at least partially disposed about the medical device and the retractable sleeve is further at least partially disposed about the retaining device.

11. The delivery system of claim 1 wherein the retractable sleeve is constructed and arranged to maintain the medical device in the pre-delivery configuration for a duration of time sufficient to move the catheter through a body lumen and into a desired position.

12. A delivery system for implantation of a medical device in a vessel, comprising:
    an elongate flexible catheter having proximal and distal ends for delivering a self-expanding medical device to a desired location in a vessel;
    a self-expanding medical device having proximal and distal ends, the medical device surrounding and carried by the flexible catheter near the distal end of said catheter, the medical device being in a delivery configuration where the medical device has a reduced radius along an axial length of said medical device;
    a remotely operable retractable sleeve surrounding the distal end of the catheter, the retractable sleeve at least partially disposed about the medical device, the retractable sleeve capable of being removed after implantation of the catheter into a body lumen;
    a retaining and storage sleeve for retaining the medical device in approximately or substantially the delivery configuration, the retaining and storage sleeve being adapted for removal from the elongate flexible catheter prior to implantation of the catheter, the retaining and storage sleeve being at least partially disposed about the retractable outer sleeve.

13. The delivery system of claim 12 wherein the retaining and storage sleeve is made of a biocompatible polymeric material.

14. The delivery system of claim 13 wherein the biocompatible polymeric material is selected from the group consisting of polyimides, teflons, polyolefins, and nylons.

15. The delivery system of claim 13 wherein the retaining and storage sleeve is made of a biocompatible metal alloy.

16. The delivery system of claim 15 wherein the biocompatible metal alloy is selected from the group consisting of stainless steel, titanium, tantalum, nitinol, and elgiloy.

17. The delivery system of claim 12 wherein the retaining and storage sleeve further comprises a proximal end, a distal end and an end cap located at the distal end.

18. The delivery system of claim 12 wherein the retaining and storage sleeve further comprises a proximal end and a distal end, the sleeve retaining and storage sleeve being enlarged at the distal end thereof.

19. The delivery system of claim 12 further including means for removing the retaining and storage sleeve.

20. A delivery system for implantation of a medical device in a vessel, comprising:
    an elongate flexible catheter having proximal and distal ends for delivering a medical device to a location in a vessel;
    a medical device having proximal and distal ends, the medical device being at least partially disposed about the flexible catheter near the distal end of said catheter, the medical device being in a delivery configuration where the medical device has a reduced radius along an axial length of said catheter;
    a retaining and storage sleeve for retaining the medical device in approximately or substantially the delivery configuration, the retaining and storage sleeve comprising a sleeve for retaining the medical device in said delivery configuration for a predetermined length of time, the sleeve at least partially disposed about the medical device, said retaining and storage sleeve being removed prior to insertion of the distal end of the catheter into a body lumen;

a retractable sleeve at least partially disposed about the retaining device.

* * * * *